United States Patent
Thakur et al.

(10) Patent No.: US 10,595,739 B2
(45) Date of Patent: Mar. 24, 2020

(54) ESTIMATING THE PREVALENCE OF ACTIVATION PATTERNS IN DATA SEGMENTS DURING ELECTROPHYSIOLOGY MAPPING

(71) Applicant: Boston Scientific Scimed Inc., Maple Grove, MN (US)

(72) Inventors: Pramodsingh Hirasingh Thakur, Woodbury, MN (US); Shibaji Shome, Arden Hills, MN (US); Allan C. Shuros, St. Paul, MN (US); Shantha Arcot-Krishnamurthy, Sammamish, WA (US); Barun Maskara, Princeton Jct, NJ (US); Sunipa Saha, Shoreview, MN (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 185 days.

(21) Appl. No.: 15/651,211

(22) Filed: Jul. 17, 2017

(65) Prior Publication Data
US 2017/0311834 A1 Nov. 2, 2017

Related U.S. Application Data

(62) Division of application No. 14/471,477, filed on Aug. 28, 2014, now Pat. No. 9,737,227.
(Continued)

(51) Int. Cl.
*A61B 5/04* (2006.01)
*A61B 5/042* (2006.01)
(Continued)

(52) U.S. Cl.
CPC ............ *A61B 5/0422* (2013.01); *A61B 5/743* (2013.01); *G06N 5/047* (2013.01); *G16H 50/20* (2018.01); *A61B 5/6858* (2013.01)

(58) Field of Classification Search
CPC ...... A61B 5/0422; A61B 5/743; A61B 5/6858; G16H 50/20; G06N 5/047
See application file for complete search history.

(56) References Cited

U.S. PATENT DOCUMENTS

| 4,754,753 A | 7/1988 | King |
| 4,799,493 A | 1/1989 | DuFault |

(Continued)

FOREIGN PATENT DOCUMENTS

| CN | 1253761 A | 5/2000 |
| CN | 101313334 A | 11/2008 |

(Continued)

OTHER PUBLICATIONS

Barbaro, V., et. al. Measure of Synchronisation of Right Atrial Depolarisation Wavefronts During Atrial Fibrillation. Med. Biol. Eng. Comput., 40(1): 56-62, 2002.
(Continued)

*Primary Examiner* — Allen Porter
*Assistant Examiner* — Natasha Patel
(74) *Attorney, Agent, or Firm* — Faegre Drinker Biddle & Reath LLP

(57) ABSTRACT

An anatomical mapping system including a plurality of mapping electrodes disposed in or near an anatomical structure and configured to detect activation signals of physiological activity, each of the plurality of mapping electrodes having an electrode location, and a processing system associated with the plurality of mapping electrodes, and configured to record the detected activation signals and associate one of the plurality of mapping electrodes with each recorded activation signal. The processing system further configured to determine a dominant frequency at each electrode location, and determine a wavefront vector at each electrode location based on a difference between the domi-
(Continued)

nant frequency at a first electrode location and the dominant frequency at neighboring electrode locations.

4 Claims, 6 Drawing Sheets

Related U.S. Application Data

(60) Provisional application No. 61/871,108, filed on Aug. 28, 2013.

(51) Int. Cl.
*A61B 5/00* (2006.01)
*G16H 50/20* (2018.01)
*G06N 5/04* (2006.01)

(56) References Cited

U.S. PATENT DOCUMENTS

| | | | |
|---|---|---|---|
| 5,038,791 A | 8/1991 | Collins et al. | |
| 5,158,092 A | 10/1992 | Glace | |
| 5,254,088 A | 10/1993 | Lundquist et al. | |
| 5,292,348 A | 3/1994 | Saumarez et al. | |
| 5,433,198 A | 7/1995 | Desai | |
| 5,485,849 A | 1/1996 | Panescu et al. | |
| 5,582,609 A | 12/1996 | Swanson et al. | |
| 5,598,848 A | 2/1997 | Swanson et al. | |
| 5,647,870 A | 7/1997 | Kordis et al. | |
| 5,657,755 A | 8/1997 | Desai | |
| 5,722,416 A | 3/1998 | Swanson et al. | |
| 5,810,740 A | 9/1998 | Paisner | |
| 6,016,442 A | 1/2000 | Hsu et al. | |
| 6,070,094 A | 5/2000 | Swanson et al. | |
| 6,233,491 B1 | 5/2001 | Kordis et al. | |
| 6,574,492 B1 | 6/2003 | Ben-Haim et al. | |
| 6,600,948 B2 | 7/2003 | Ben-Haim et al. | |
| 6,735,465 B2 | 5/2004 | Panescu | |
| 6,950,689 B1 | 9/2005 | Willis et al. | |
| 6,978,168 B2 | 12/2005 | Beatty et al. | |
| 7,123,954 B2 | 10/2006 | Narayan et al. | |
| 7,841,966 B2 | 11/2010 | He et al. | |
| 9,144,391 B2 | 9/2015 | Thakur et al. | |
| 9,332,920 B2 | 5/2016 | Thakur et al. | |
| 2003/0093004 A1 | 5/2003 | Sosa et al. | |
| 2005/0007091 A1 | 1/2005 | Makeig et al. | |
| 2005/0261599 A1 | 11/2005 | Shvilkin et al. | |
| 2006/0074336 A1 | 4/2006 | Grieve et al. | |
| 2006/0116594 A1 | 6/2006 | Zhang et al. | |
| 2007/0299351 A1 | 12/2007 | Harlev et al. | |
| 2008/0222109 A1 | 9/2008 | Sakurai | |
| 2010/0094274 A1 | 4/2010 | Narayan et al. | |
| 2010/0298651 A1 | 11/2010 | Moon et al. | |
| 2011/0251505 A1 | 10/2011 | Narayan et al. | |
| 2012/0184858 A1 | 7/2012 | Harlev et al. | |
| 2012/0296569 A1* | 11/2012 | Shahaf | A61B 5/048 702/19 |
| 2013/0274582 A1* | 10/2013 | Afonso | A61B 5/0422 600/374 |
| 2014/0336518 A1 | 11/2014 | Shuros et al. | |
| 2014/0343388 A1 | 11/2014 | Thakur et al. | |
| 2014/0343442 A1 | 11/2014 | Thakur et al. | |
| 2014/0371616 A1 | 12/2014 | Narayan et al. | |
| 2015/0065836 A1 | 3/2015 | Thakur et al. | |
| 2015/0230721 A1* | 8/2015 | Lo | A61B 5/04011 600/512 |
| 2015/0366476 A1 | 12/2015 | Laughner et al. | |
| 2016/0073913 A1 | 3/2016 | Francis et al. | |
| 2016/0089050 A1 | 3/2016 | Thakur et al. | |

FOREIGN PATENT DOCUMENTS

| | | |
|---|---|---|
| CN | 101317194 A | 12/2008 |
| CN | 102245091 A | 11/2011 |
| CN | 202335863 U | 7/2012 |
| CN | 105307558 A | 2/2016 |
| EP | 2996547 A1 | 3/2016 |
| GB | 13072111 | 5/2013 |
| JP | 2005131367 A | 5/2005 |
| JP | 2005237781 A | 9/2005 |
| JP | 4001959 B2 | 10/2007 |
| JP | 2007537823 A | 12/2007 |
| JP | 2008500135 A | 1/2008 |
| JP | 2008515485 A | 5/2008 |
| JP | 2009537252 A | 10/2009 |
| JP | 2012505047 A | 3/2012 |
| JP | 2013523345 A | 6/2013 |
| JP | 2014502556 A | 2/2014 |
| WO | WO2000045700 A1 | 8/2000 |
| WO | 2006066324 A1 | 6/2006 |
| WO | 2011127211 A2 | 10/2011 |
| WO | 2012092016 A1 | 7/2012 |
| WO | 2012097059 A1 | 7/2012 |
| WO | 2012151008 A2 | 11/2012 |
| WO | 2013123549 A1 | 8/2013 |
| WO | 2014100464 A1 | 6/2014 |
| WO | 2014186684 A1 | 11/2014 |

OTHER PUBLICATIONS

Berkowitsch, Alexander et al., "Electrophysiological Heterogeneity of Atrial Fibrillation and Local Effect of Propafenone in the Human Right Atrium: Analysis Based on Symbolic dynamics", Journal of Interventional Cardiac Electrophysiology, Jun. 1, 2000, pp. 383-394.

Brodda, K., et. al. A New Method for Detection of P Waves in Electrocardiograms. Signal Processing, 1(1): 15-25, 1979.

Ciaccio, Edward J. et al., "Identification of recurring patterns in fractionated atrial electrograms using new transform coefficients", Biomedical engineering Online, vol. 11, No. 1, Jan. 1, 2012, 19 pages.

Fitzgerald, Tamara N. et all, "Identification of Cardiac Rhythm Features by Mathematical Analysis of Vector Fields", IEEE Transactions on Biomedical Engineering, vol. 52, No. 1, Jan. 2005, pp. 19-29.

Habel, N., et. al. The Temporal Variability of Dominant Frequency and Complex Fractionated Atrial Electrograms Constrains the Validity of Sequential Mapping in Human Atrial Fibrillation, Heart Rhythm, 7:586-593, 2010.

Holm, Magnus et al. A New Method for Analysis of Atrial Activation During Chronic Atrial Fibrillation in Man. IEEE Transactions on Biomedical Engineering, 43(2): 198-210, Feb. 1996.

Houben, R. P. M., et. al. Processing of Intracardiac Electrograms in Atrial Fibrillation: Diagnosis of Electropathological Substrate of AF. IEEE Engineering in Medicine and Biology Magazine, 25(6):40-51, Nov. 1, 2006.

Houben, Richard P.M. et al., "Processing Intracardiac Electrograms in Atrial Fibrillation", Diagosis of Electropathological Substrate of AF, IEEE Engineering in Medicine and Biology Magazine, Nov./Dec. 2006, pp. 40-51.

International Preliminary Report on Patentability issued in PCT/US2013/076667, dated Jul. 2, 2015, 9 pages.

International Preliminary Report on Patentability issued in PCT/US2014/038357, dated Nov. 26, 2015, 8 pages.

International Preliminary Report on Patentability issued in PCT/US2014/053147, dated Mar. 10, 2016, 9 pages.

International Preliminary Report on Patentability issued in PCT/US2014/062876, dated May 12, 2016, 9 pages.

International Preliminary Report on Patentability issued in PCT/US2015/036746, dated Dec. 20, 2016, 8 pages.

International Search Report and Written Opinion issued in PCT/US2014/038357, dated Sep. 1, 2014, 11 pages.

International Search Report and Written Opinion issued in PCT/US2013/076667, dated Mar. 20, 2014, 14 pages.

International Search Report and Written Opinion issued in PCT/U52014/062876, dated Feb. 11, 2015, 12 pages.

International Search Report and Written Opinion issued in PCT/US2015/036746, dated Sep. 1, 2015, 12 pages.

(56) References Cited

OTHER PUBLICATIONS

International Search Report and Written Opinion] issued in PCT/US2014/053147, dated Nov. 7, 2014, 12 pages.
Jadidi, A., et. al. Functional Nature of Electrogram Fractionation Demonstrated by Left Atrial High-Density Mapping. Circ. Arrhythm Electrophysiol., 5:32-42, 2012.
Marbroukeh, Nizar R. et al., "A Taxonomy of Sequential Pattern Mining Algorithms", ACM Computing Surveys, vol. 43, No. 1, Nov. 1, 2010, pp. 1-41.
Masse, Stephane et al., "Wave similarity of human ventricular fibrillation from bipolar electrograms", Europace, vol. 9, No. 1, Jan. 1, 2007, 10 pages.
Masse, Stephane, et al. "Ventricular Fibrillation in Myopathic Human Hearts: Mechanistic Insights From in Vivo Global Endocardial and Epicardial Mapping." Am. J. Physiol. Heart Circ. Physiol. 292:H2589-H2597, 2007.
Rogers, Jack m et al., Recurrent Wavefront Morphologies: A Method for Quantifying the Complexity of Epicardial Activation Patterns, Annals of Biomedical Engineering, vol. 25, No. 5, 1997, pp. 761-768.
Sanders et al., "Spectral Analysis identifies Sites of High-Frequency Activity Maintaining Atrial Fibrillation in Humans", Circulation, 112:789-797, 2005.
Tseng, Vincent; et al. "Effective Temporal Data Classification by Integrating Sequential Pattern Mining and Probabilistic Induction." Expert Systems With Applications 36:9524-9532, 2009.

\* cited by examiner

ESTIMATING THE PREVALENCE OF ACTIVATION PATTERNS IN DATA SEGMENTS DURING ELECTROPHYSIOLOGY MAPPING

CROSS-REFERENCE TO RELATED APPLICATION

This application is a division of U.S. application Ser. No. 14/471,477, filed Aug. 28, 2014, which claims priority to U.S. Provisional Application No. 61/871,108, filed Aug. 28, 2013, which is herein incorporated by reference in its entirety.

TECHNICAL FIELD

The present disclosure relates to cardiac mapping systems. More specifically, the present disclosure relates to a cardiac mapping system configured to identify and classify activation signal patterns during electrophysiological studies.

BACKGROUND

Diagnosing and treating heart rhythm disorders often involves the introduction of a catheter having a plurality of sensors/probes into a cardiac chamber through the surrounding vasculature. The sensors detect electric activity of the heart at sensor locations in the heart. The electric activity is generally processed into electrogram signals that represent signal propagation through cardiac tissue at the sensor locations.

Systems can be configured to display the electrical signals detected in the cardiac chamber as an activation map based on voltages detected. Patterns in the displayed activation signals can be useful for detection regions associated with a pathophysiology. However, these activation patterns can be complex and vary greatly amongst sensed activation signals thus making the task of identifying patterns increasingly difficult. There exists a need to identify prevalent patterns in complex activation signal patterns to get an overall survey of a patient's health.

SUMMARY

In Example 1, a method for mapping an anatomical structure includes sensing activation signals of physiological activity with a plurality of mapping electrodes disposed in or near the anatomical structure, each of the plurality of mapping electrodes having an electrode location, identifying patterns among the sensed activation signals representing activation propagation, generating a similarity measure between each unique pair of identified patterns, and classifying the patterns into groups based on the similarity measure.

In Example 2, the method according to Example 1, further includes determining a characteristic representation for each group, and displaying a summary plot based on the characteristic representation for each group.

In Example 3, the method according to either of Examples 1 and 2, wherein the characteristic representation includes at least one of a mean, variance, covariance, standard deviation, median, and prevalence.

In Example 4, the method according to any one of Examples 1-3, wherein identifying patterns further includes generating a pattern map for each sensed activation signal, each pattern map having at least one of a vector field map that represents a direction and magnitude of activation signal propagation, a voltage propagation map that represents a direction and magnitude of voltage propagation, a phase propagation map that represents a direction and magnitude of phase propagation, and an action potential duration map that represents a duration of an action potential.

In Example 5, the method according to any one of Examples 1-4, wherein the patterns classified into groups are compared with at least one pattern template for each of the groups.

In Example 6, the method according to any one of Examples 1-5, wherein identifying patterns further includes identifying unclassifiable patterns that are not classifiable into any groups of similar patterns, and determining a measure of randomness based on the unclassifiable patterns.

In Example 7, the method according to any one of Examples 1-6, wherein generating the similarity measure further includes generating a similarity matrix including the patterns, each entry of the similarity matrix representing the similarity measure for each unique pair of identified patterns generated based on a correlation of the corresponding patterns.

In Example 8, the method according to any one of Examples 1-7, wherein classifying the patterns further includes determining a correlation coefficient for each unique pair of patterns, and classifying the patterns into distinct groups based on a percentage of patterns among each group having a particular correlation coefficient.

In Example 9, a method for mapping cardiac tissue, comprising sensing activation signals of cardiac activity with a plurality of mapping electrodes disposed in or near the cardiac tissue, each of the plurality of mapping electrodes having an electrode location, identifying patterns among the sensed activation signals, generating a similarity measure between each of unique pairs of identified patterns, classifying the patterns into groups based on similarity measure, determining a characteristic representation for each group of the groups, and displaying a summary plot of one or more characteristic representations.

In Example 10, the method according to Example 9, wherein the characteristic representation includes at least one of a mean, variance, covariance, standard deviation, median, and a prevalence of the pattern.

In Example 11, the method according to of Examples 9 and 10, further comprising generating a plurality of pattern maps for each activation signal, each pattern map having at least one of a vector field map which represents a direction and a magnitude of an activation signal propagation, a voltage propagation map which representation a direction and a magnitude of voltage propagation, a phase propagation map which represents a direction and a magnitude of phase propagation, and an action potential duration map which represents a duration of an action potential.

In Example 12, the method according to any one of Examples 9-11, wherein generating the plurality of pattern maps further includes identifying unclassifiable pattern maps that are not classifiable into any groups of similar patterns, and determining a measure of randomness based on the unclassifiable pattern maps.

In Example 13, the method according to any one of Examples 9-12, wherein generating the similarity measure further comprises generating a similarity matrix including the patterns, each entry of the similarity matrix representing the similarity measure for each unique pair of identified patterns generated based on a correlation of the corresponding patterns.

In Example 14, the method according to any one of Examples 9-13, wherein classifying the patterns further comprises determining a correlation coefficient for each unique pair of patterns, and classifying the patterns into distinct groups based on a percentage of patterns among each group having a particular correlation coefficient.

In Example 15, an anatomical mapping system comprising a plurality of mapping electrodes disposed in or near an anatomical structure configured to detect activation signals of physiological activity, each of the plurality of mapping electrodes having an electrode location, and a processing system associated with the plurality of mapping electrodes, the processing system configured to record the detected activation signals and associate one of the plurality of mapping electrodes with each recorded activation signal, the processing system further configured to determine a dominant frequency at each electrode location, and determine a wavefront vector at each electrode location based on a difference between the dominant frequency at a first electrode location and the dominant frequency at neighboring electrode locations.

In Example 16, the anatomical mapping system according to Example 15, wherein the processing system is further configured to determine a characteristic representation of one or more similarity measures, and display a summary plot of the characteristic representations.

In Example 17, the anatomical mapping system according to either of Examples 15 and 16, wherein the processing system is further configured to generate a plurality of pattern maps, and wherein, to generate the plurality of pattern maps, the processing system is further configured to generate a pattern map for each sensed activation signal, each pattern map having at least one of a vector field map comprising of wavefront vector at each electrode location.

In Example 18, the anatomical mapping system according to any of Examples 15-17, wherein generating the plurality of pattern maps includes identifying unclassifiable pattern maps that are not classifiable into any groups of similar patterns and determining a measure of randomness based on the unclassifiable pattern maps.

In Example 19, the anatomical mapping system according to any of Examples 15-18, wherein the processing system is further configured to generate a similarity measure based on each unique pair of identified patterns generated, which are based on a correlation of the corresponding patterns.

In Example 20, the anatomical mapping system according to any of Examples 15-19, wherein the similarity measure is a correlation coefficient between each unique pair of pattern maps.

In Example 21, the anatomical mapping system according to any of Examples 15-17, further comprising classifying patterns into distinct groups based on a percentage of patterns within each group having a particular similarity measure.

In Example 22, a method for mapping an anatomical structure, the method comprising sensing activation signals of physiological activity with a plurality of mapping electrodes disposed in or near the anatomical structure, determining a reference location and a corresponding segmented block for each instance of the physiological activity in the sensed activation signals, and iteratively classifying segmented blocks into groups and simultaneously refining the reference location used for the segmented block.

In Example 23, the method of Example 22, further comprising determining a characteristic representation for each group and displaying a summary plot of the characteristic representations.

In Example 24, the method of either of Examples 22 and 23, wherein iteratively classifying the segmented blocks into groups further comprises, iteratively, initializing a first and a second cluster, wherein the first cluster includes segmented blocks and the second cluster is empty, determining a characteristic representation of the segmented blocks in the first and second clusters, populating the second cluster with segmented blocks from the first cluster that do not meet a similarity measure threshold between each reference segment and the characteristic representation, updating the characteristic representation based on remaining segmented blocks, and populating the first cluster with segmented blocks from the first cluster that meet the updated similarity measure threshold between each segmented block and the updated characteristic representation.

In Example 25, the method of any of Examples 22-24, further comprising repeating the steps of populating the first and second clusters and updating the characteristic representation until the second cluster cannot be populated with segmented blocks from the first cluster and the first cluster cannot be populated with segmented blocks from the second cluster, and labeling the first cluster as a new optimized cluster, wherein the segmented blocks in the optimized cluster are identified as optimal segmented blocks for each corresponding instance of physiological activity.

In Example 26, the method of any of Examples 22-25, further comprising initializing a new first cluster, wherein the new first cluster includes remaining segmented blocks from the second cluster, initializing a new second cluster, wherein the new second cluster is empty, and repeating the steps of populating the clusters, updating the characteristic representation, labeling new optimized clusters, and initializing new clusters until optimized clusters cannot be labeled.

In Example 27, the method of any of Examples 22-26, wherein the optimal segmented blocks are identified independent of determining activation times for the sensed activation signals.

In Example 28, the method of any of Examples 22-27, wherein the characteristic representation is a mean of the corresponding segmented blocks.

In Example 29, the method of any of Examples 22-28, further comprising determining a plurality of segmented block candidates corresponding to a plurality of determined reference locations, determining an optimal segmented block for each reference location based on maximizing a similarity measure between the segmented block candidates and the corresponding characteristic representation, updating the reference location based on the reference location corresponding to the optimal segmented block to obtain an updated reference location, and updating the segmented block based on the updated reference location.

In Example 30, the method of any of Examples 22-29, wherein determining a plurality of segmented block candidates further comprises determining a minimum reference location and maximum reference location based on a maximum lag value from a current reference location with equally spaced time steps therebetween, and defining a segmented block candidate at each time step based on a corresponding segmented block, wherein each segmented block candidate is temporally shifted from the reference location based on the corresponding time step.

In Example 31, the method of any of Examples 22-30, wherein each optimal segmented block is determined based on a comparison of each corresponding segmented block candidate to the characteristic representation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
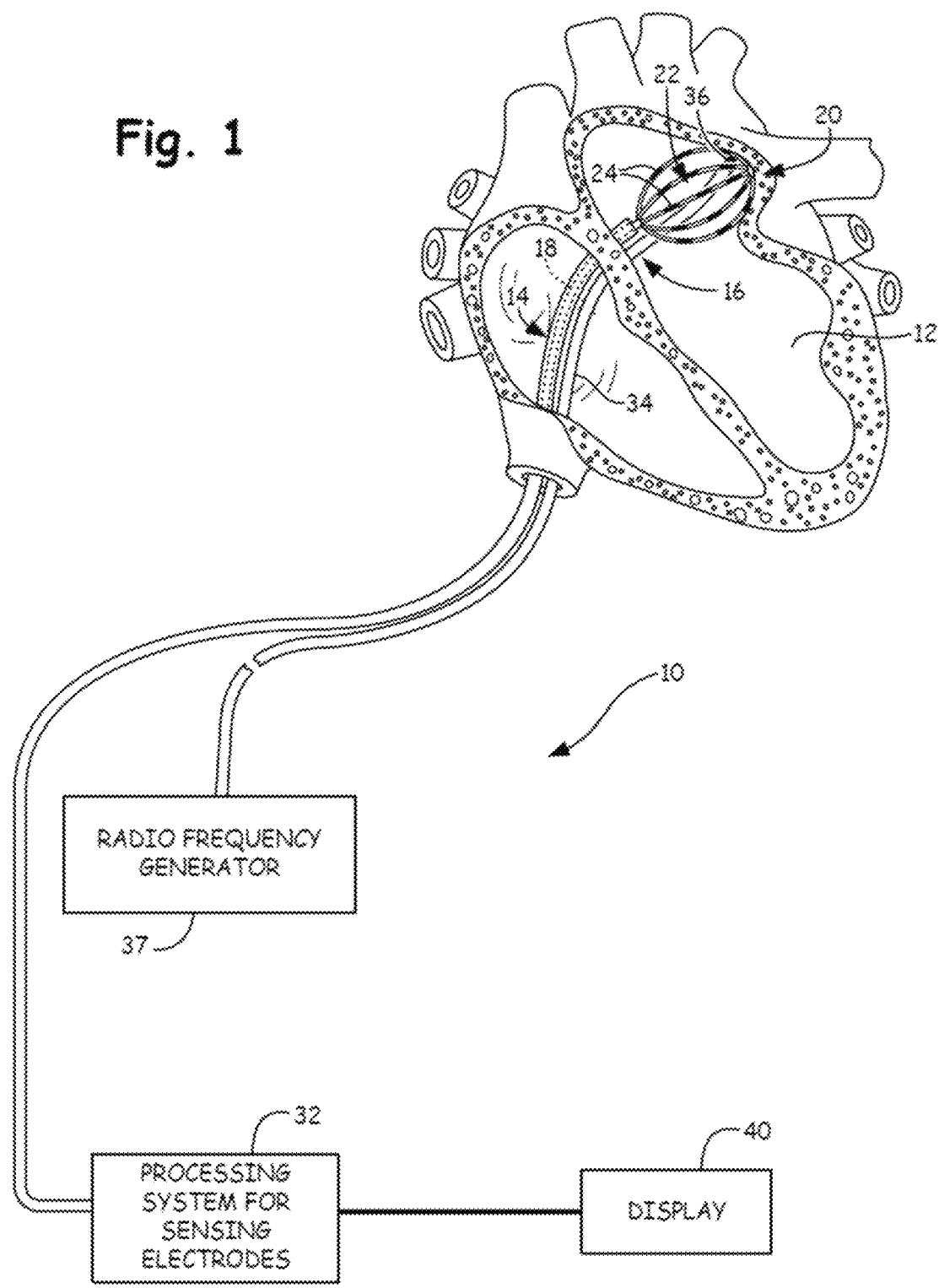
FIG. 1 is a schematic view of an embodiment of a system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes 24 are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas the far-field signal component includes activation signals originating from the ventricular myocardial tissue. The near-field activation signal component can be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. Studies have shown that dominant rotors and/or divergent activation patterns have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristics, such as an APD map, a vector field map, a contour map, a reliability map, a conduction velocity map, an electrogram, and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a device 40 the display of relevant characteristics for viewing by a physician. In the illustrated embodiment, device 40 is a CRT, LED, or other type of display, or a printer). The device 40 presents the relevant characteristics in a format most useful to the physician. In addition, the processing system 32 may generate position-identifying output for display on the device 40 that aids the physician in guiding the ablation electrode(s) 36 into contact with tissue at the site identified for ablation.

Figure 2:
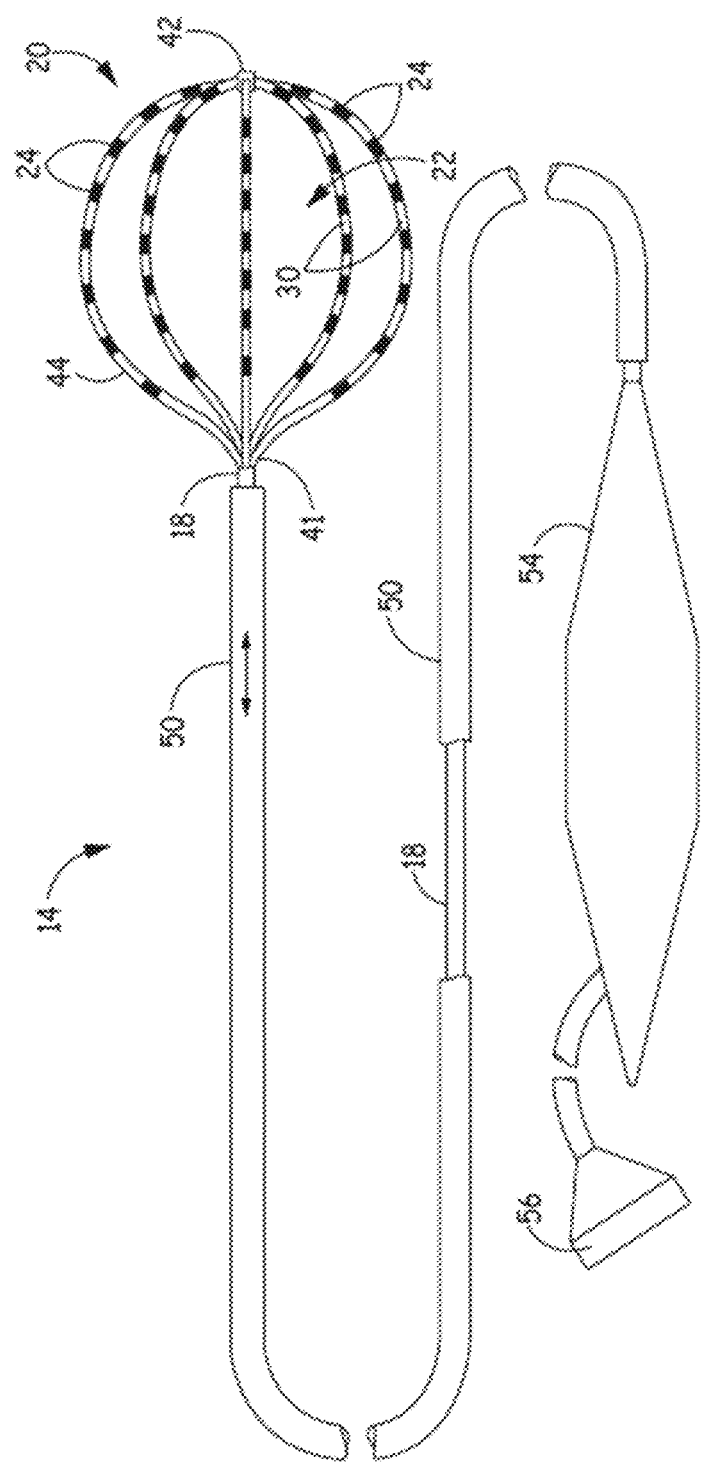
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 is movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby expressly incorporated herein by reference in its entirety.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system (not shown). As another example, the ablation electrode at the distal end of the ablation catheter may be coupled to the signal processing system 32 to also operate as a mapping electrode.

Figure 3:
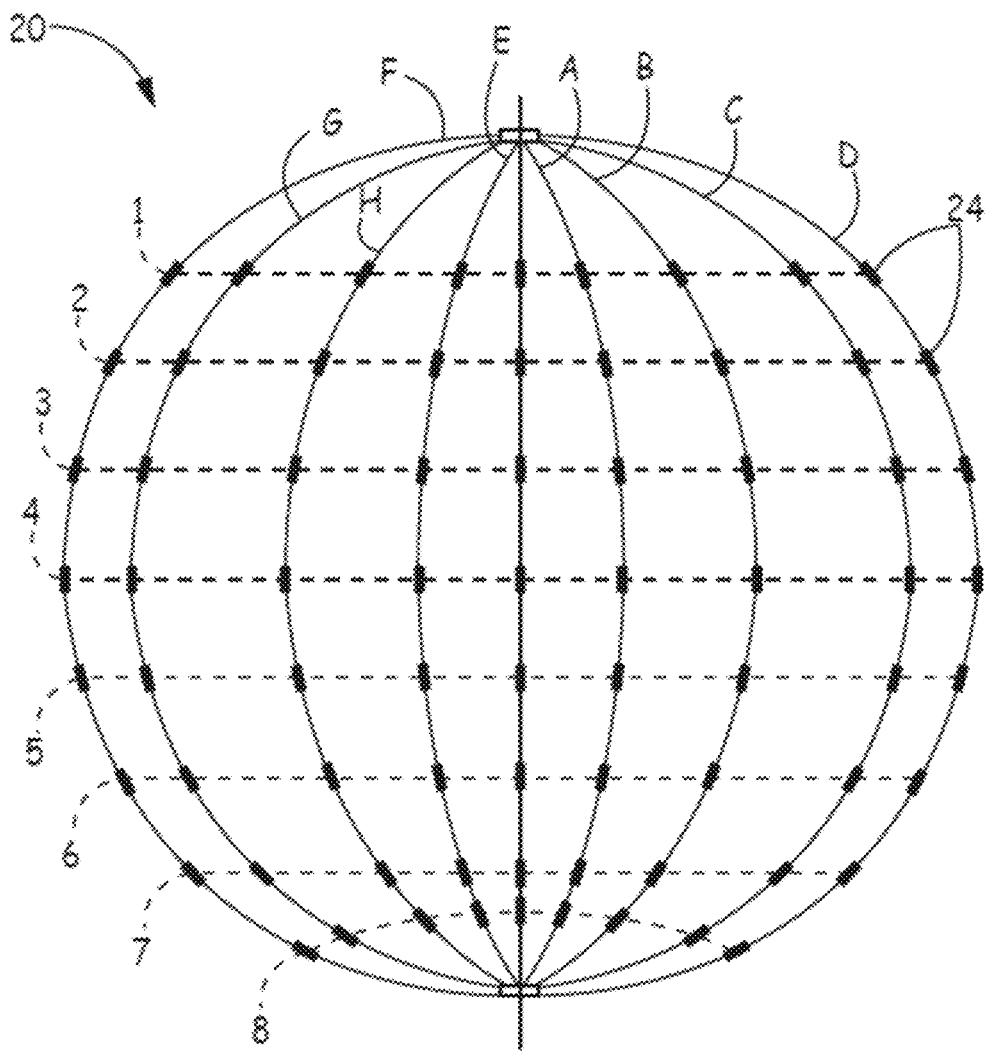
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned inside of, or otherwise adjacent to the anatomical structure to be treated (e.g., left atrium or left ventricle of the heart), the processing system 32 is configured to record the activation signals from each electrode 24 channel related to intrinsic physiological activity of the anatomical structure, i.e. the electrodes 24 measure electrical activation signals intrinsic to the physiology of the anatomical structure.

In some embodiments, the processing system 32 is configured to identify and display prevalent patterns in a data stream of sensed activation signals. The processing system 32 generates a pattern map based on the sensed activation signals. The pattern map includes at least one of a vector field map which represents a direction and magnitude (or velocity) of propagation of a sensed activation signal, a voltage propagation map such as a contour map of isopotential lines which representation a direction and magnitude of voltage propagation at each electrode location, a phase propagation map such as a contour map of iso-phase lines which represents a direction and magnitude of signal phase propagating at each electrode location, a derivative map which illustrates the change in voltage over time at each electrodes location, an action potential duration map which represents a duration of an action potential, any combination thereof, and the like. In some embodiments, the processing system 32 generates pattern maps based on sensed activation signals sensed from a subset of mapping electrodes 24. This arrangement can be useful to optimize computation cycles and/or time. The processing system 32 can then identify prevalent patterns based on the subset of sensed activation signals. In an additional aspect, processing system 32 may generate one or more similarity measures that represent a correlation between patterns, which may, in some examples, constitute a similarity vector indicating an angle and distance between patterns as a vector representation in multi-dimensional space. Furthermore, the processing system 32 can combine structured datasets, similarity measures and/or similarity vectors, and characteristic representations (which will be discussed in further detail) from distinct or overlapping subsets to generate a composite representation.

For example, the vector field map includes a plurality vectors wherein each vector is associated with each electrode 24 and represents a local direction of propagation of the sensed activation signals sensed at the corresponding electrode 24 location with respect to an adjacent or neighboring electrode 24. To determine each vector which corresponds to a propagating activation signal at an electrode location, the processing system 32 calculates a circular average of detected activation signals at adjacent or neighboring electrodes 24 according to a time difference between an activation signal sensed at a current electrode location and the activation signal sensed at a neighboring electrode location. The process is repeated at each electrode location for each sensed activation signal to generate a series of consecutive grids or fields of vectors wherein each vector corresponds to a mapping electrode 24 and each vector field represents at least each sensed activation signal and possibly quiescent periods. Other types of pattern maps, such as, but not limited to, the voltage propagation map, phase propagation map, derivative map, action potential duration map, and the like are generated in similar fashion as necessary generate the desired pattern map.

The processing system 32 is configured to identify a pattern for each generated pattern map. Each pattern map can be compared to one or more of a plurality of pattern templates which are stored within a template bank. The template bank can be a database, an array, or a plurality of pattern templates that are stored locally in memory in the processing system 32 or can be stored in a remote location and accessed via a network or internet connection. Each pattern template includes a pattern having a location associated therewith. For example, the pattern may include patterns related to identifying a dominant rotor and/or divergent activation pattern associated with cardiac fibrillation. Each pattern template may include a unique pattern having an associated location include, for example, a curled pattern which can represent rotor activity including a rotor core and/or rotor path having a core location or a divergent pattern representing focal activity having a foci location.

The processing system 32 stores the identified patterns in a structure data set, such as a multi-dimensional database or multi-dimensional matrix, such that each pattern is associated with a data set location which corresponds to the pattern map from which the pattern is identified. After the structured data set is populated with the identified patterns, the processing system 32 generates a similarity measure for each unique pair of identified patterns. One example of a similarity measure is a correlation between each unique pair of patterns or pattern maps. After each unique pair of patterns are assigned a similarity measure, the processing system 32 classifies all observed patterns into at least one group or into distinct groups based on the similarity measure. For instance, pattern maps with high similarity measure are grouped into the same group, whereas pattern maps with low similarity measures are grouped into different groups. The correlation function employed by the processing system 32 may include, but not limited to, a cross-correlation, a normalized correlation, a phase correlation, a degree of coherence, cross-covariance, a correlation coefficient, or any measure that can be used to examine the relationship between a pair of pattern maps. For example, if a cross-correlation function is employed by the processing system 32 to group the observed pattern maps and correlation coefficient is determined between each pair of pattern maps, then the processing system can group similar vectors together based on the determined correlation coefficient such as establishing minimum and/or maximum correlation coefficient threshold for each group for which a correlation coefficient falls within. The grouping can also be based on a percentage of pattern maps among each group with which each member pattern map satisfies the pair-wise correlation coefficient threshold. For example, the processing system 32 may form groups of pattern maps such that each pattern map in a given group has at least 0.7 correlation with at least 75% of the other pattern maps in the same group. The grouping could also be based on degree of dissimilarity based on a low similarity measure. For example, if a given pattern has correlation less than a certain threshold, with a majority of the patterns belonging to a particular group, then the pattern is declared to be not belonging to that group and is placed in a separate group. Continuing with the example of the correlation coefficient grouping function, the processing system 32 may limit the number of similar patterns per group. If a group is too large or too small, the processing system 32 adjusts the minimum and/or maximum correlation threshold associated with the corresponding group.

In some embodiments, the processing system 32 determines a characteristic representation for each group. The processing system 32 is configured to identify and display the most prevalent patterns among the sensed activation signals. The size of each classified or determined group of similar patterns corresponds to the prevalence of the characteristic pattern represented by that group. The characteristic representation is a single representation assigned to the corresponding group to summarize the associated similar patterns to aid an efficient and useful visualization. The characteristic representation may include a mean of some or all of the patterns classified within each group. The characteristic representation is not limited to an average or mean, it may include a median, mode, a standard deviation, and the like. The determined characteristic representation is displayed on the display device 40 for inspection by a user or a physician to diagnose or detect a pathophysiological condition in the anatomical structure and the size of the group is presented as an indication of prevalence of that pattern.

Figure 4:
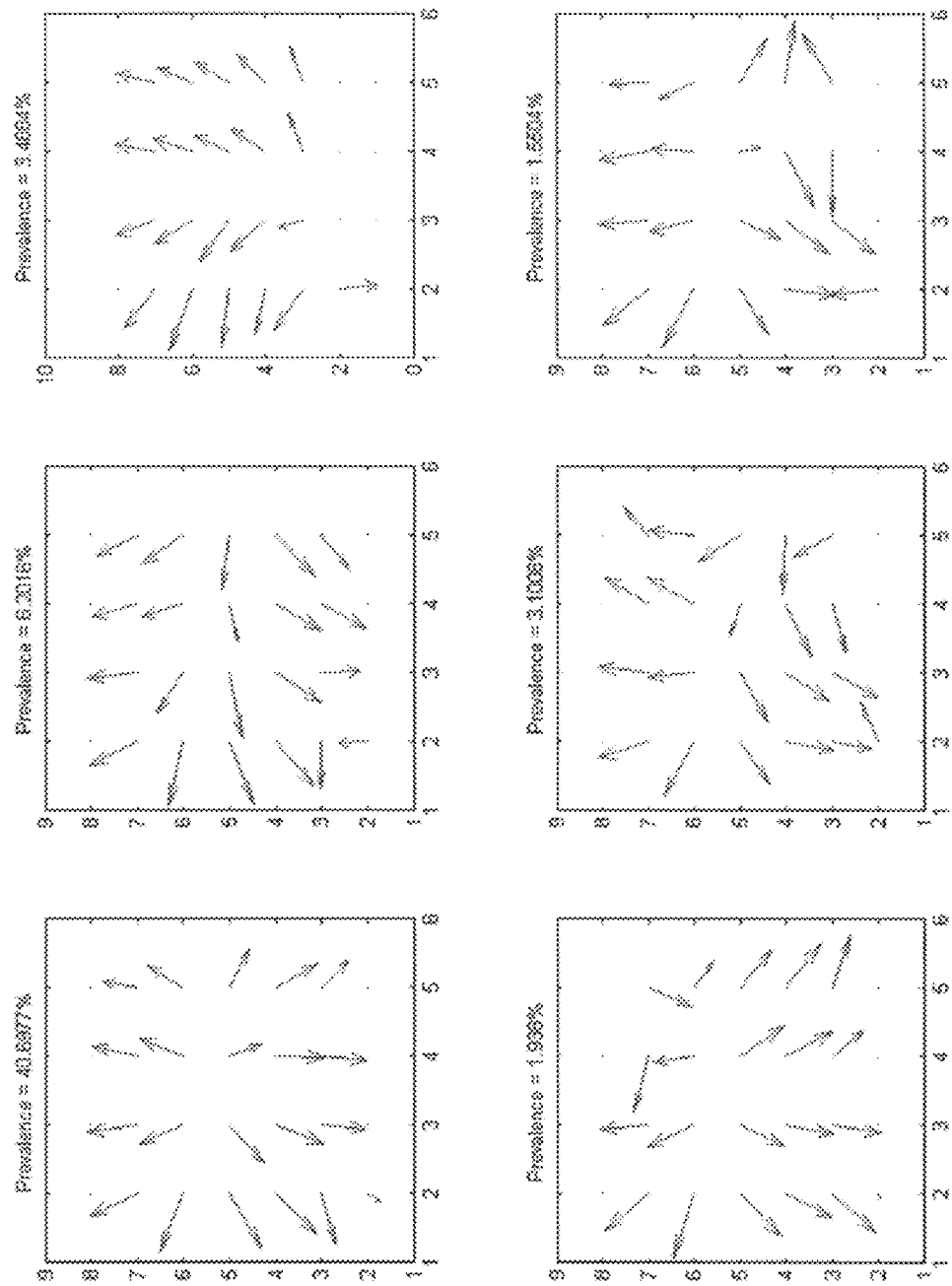
FIG. 4 is a plurality of identified characteristic representations of propagation patterns.
Figure 5:
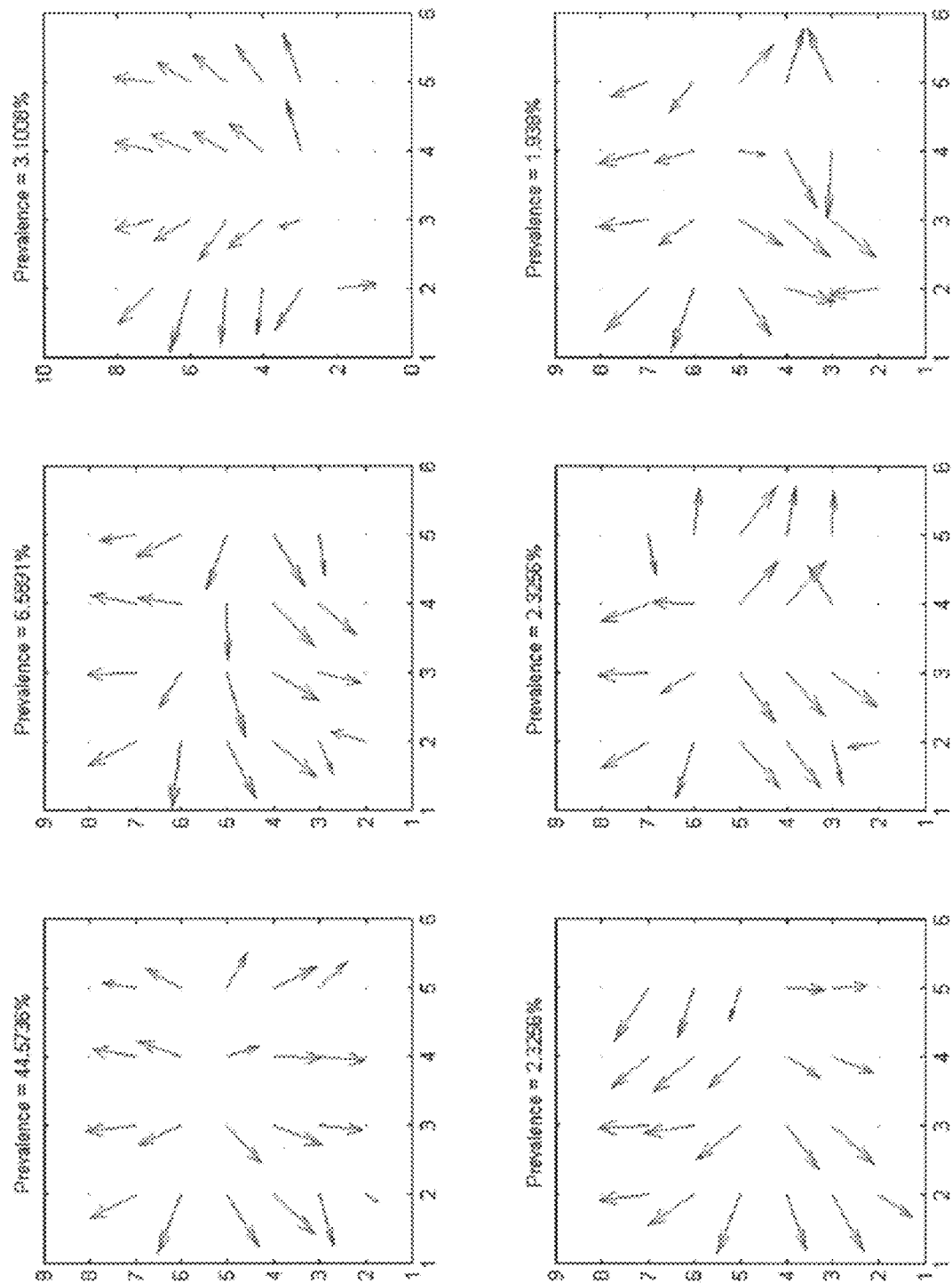
FIG. 5 is a plurality of identified characteristic representations of propagation patterns.

FIGS. 4 and 5 illustrate a displayed characteristic representation of identified groups during aberrant cardiac activation, e.g. fibrillation, including a percentage of prevalence for each classified and characterized group of similarity measures and/or related similarity vectors. In some embodiments, the processing system 32 is configured to generate a user interface which allows a user or physician to generate a display of all of the identified and classified patterns or to display a selected number of the most prevalent identified and classified patterns. The user interface may include separate panels for different regions during sequential mapping for cross-comparison of most prevalent patterns in different regions. The user interface can include a simple push-button implementation which can display parameter selection interface in which the user selects parameters for display on the user interface and display device related to, for example, a summary plot along with prevalence information for each pattern. The parameter selection interface may include a user selectable threshold for displaying the previously described most prevalent identified and classified patterns.

Furthermore, in the methods described above, it is implicitly assumed that activations of the recorded physiologic signals are detectable and patterns of activation propagation between electrodes are constructable. However detecting activations is complex, especially during atrial fibrillation where electrical activity can be aberrant to the point on being non-deterministic. Thus, detecting individual activation times is challenging and can introduce errors that can produce erroneous pattern maps resulting in poor clustering and prevalence estimation. To minimize such erroneous pattern map production, in some embodiments, the processing system 32 may segment multi-electrode signal data into data blocks based upon some global reference or fiducial and cluster these data blocks instead of pattern maps derived out of detected activations. For example, the processing system could segment T time samples around each reference across the M×N electrodes to yield signal blocks of sizes T×M×N. A user can input a segmentation length, i.e. the number of time steps before and after the corresponding initial reference point, or the segmentation length can be automatically assigned by the processing system 32 based on a priori data or knowledge regarding hear beat lengths or corresponding physiological events.

One example of the global reference used to segment the multi-electrode signal is a heart beat, i.e., atrial or ventricular beat. In one example, the processing system 32 calculates the root mean square (RMS) of the data stream activation signals across all electrodes 24 and identifies the peaks in the RMS data stream as the global beat reference or fiducial. In another instance the processing system 32 determines activation times corresponding to a particular beat on each channel and takes the average activation time across all channels as the global reference for that beat.

Clustering temporal blocks of data segmented based on some global reference can be very sensitive to the choice of reference. Any errors in references can introduce errors by making similar signal look different due to an offset in references. This limitation, however, can be overcome by incorporating an iterative refinement of the fiducial reference for each beat as resultant segments are clustered into groups. Therefore, the processing system 32 is configured to estimate an initial reference point for each beat, or instance of physiological activity, and iteratively or dynamically refine the reference point while clustering the segmented beats into groups using the data stream of sensed activation signals from the plurality of mapping electrodes 24 independent of determining onset times for the sensed activation signals.

The processing system 32 determines an initial reference point or location for each heart beat. In one example, the processing system 32 calculates the root mean square (RMS) of the data stream activations signals across all electrodes 24 and identifies the peaks in the RMS data stream. The initial reference point acts as a starting point or initial estimate which the processing system 32 can use to segment the data stream into consecutive reference segments that represent individual heart beats. The processing system 32 initializes two groups or clusters of blocks, a first group or Current Group (CurrGr) and a second group or an Unclassified Group (UG). The processing system populates CurrGr with all of the initial segmented blocks and iteratively shrinks the number of blocks in the cluster according to a predetermined set criteria or threshold established manually by a user or automatically by the processing system 32. One of the predetermined criteria could be based on a comparison with a characteristic representation or template block for that group. The template block can be formed by taking an average of all blocks in CurrGr. If any block does not meet the criteria (of certain level of similarity with the template block), it is placed into the UG cluster. As previously described, the processing system dynamically refines the reference points of each segmented block. This can be achieved by dynamically or iteratively adjusting the predetermined criteria based on inclusivity and/or exclusivity of blocks in the CurrGr cluster. After each iteration of shrinking the CurrGr cluster, the template block is updated based on the remaining blocks in the CurrGr cluster. This is followed by a growing iteration in which signal blocks in the UG cluster that meet the similarity criteria with the newly updated template block are repopulated back into the CurrGr cluster. The shrinking and growing iterations are repeated until CurrGr and UG clusters have stabilized or reached a steady state condition in which no blocks in CurrGr are below the current threshold of similarity with the template block and no blocks in UG exceed the current threshold of dissimilarity with the template block.

In some embodiments, the processing system can be configured to compare each segmented block (based on the corresponding initial reference) and corresponding plurality of "shifted" segment blocks based on a plurality of candidate references to a characteristic representation of CurrGr (or the template). The reference candidates are references that are temporally shifted in both directions from the initial references to determine the optimal reference for each segmented block. For example, if a maximum lag value L is chosen for the number of time steps preceding and following the corresponding initial references, then there will be 2L shifted block candidates plus the initial reference resulting in a total of 2L+1 total number of segmented blocks compared to the characteristic representation. If one of the shifted candidates yields a higher degree of similarity to the characteristic representation, then the initial reference of the corresponding segmented block is updated by the reference of the best matching block and thus temporally shifting the resultant segmented block accordingly.

The processing system 32 can determine an initial characteristic representation (ICR) of the CurrGr cluster based on the determined initial references for each of the segmented blocks. For example, the characteristic representation can be an averaged reference of the segmented blocks in CurrGr, i.e. the processing system aligns the reference segments and determines an average of all of the segmented blocks since they are all initially assigned to CurrGr. An average or mean is one example of a characteristic representation while other characteristic representation are also contemplated, such as a standard deviation, a maximum/minimum, frequency domain representations, and the like.

The processing system also determines all of the potential references that correspond to each initial reference based on a selected maximum lag L which can be manually selected or automatically selected by the processing system based on a priori training data or knowledge. The processing system compares the 2L+1 references (i.e. both the initial reference and reference candidates) for each block of the data stream to the initial characteristic representation (ICR) via a similarity algorithm such as a cross-correlation or any other suitable similarity measure or index such as a distance measure or the like. If none of the calculated similarity indices corresponding to segmented block meets a preselected or predetermined threshold, the block is reclassified into the UG cluster. If more than one of the 2L+1 references meets or exceeds the threshold, the processing system determines which references has the highest or maximum degree of similarity to the ICR. If the initial reference is determined to be most similar to the ICR, then the corresponding block remains classified in CurrGr and the ICR remains unchanged. If one of the reference candidates is determined to have the highest degree of similarity to the ICR, then the corresponding segmented block (based on the initial reference) is replaced with a temporally shifted segmented block which is shifted based on the temporal relationship of the reference candidate to the initial reference, e.g. if the reference candidate is shifted 2 time steps proceeding the initial reference, then the segmented block is shifted 2 time steps proceeding the initial segmented block. In other words, the reference corresponding to the segmented block is updated with the optimal reference candidate, whether it is the initial reference or one of the reference candidates. Furthermore, the ICR is updated based on the replaced or temporally shifted block of segmented data stream, i.e. the initial segmented block is replaced with the updated segmented block and the characteristic representation is recalculated to include the updated or shifted block, and is no labeled the updated characteristic representation (UCR).

The shrinking process is repeated for each of the segmented block in the CurrGR cluster are until an optimal reference candidate is determined for each segmented block from the data stream of activation signals and until each segmented block that has no candidates (i.e. initial reference and reference candidates) that meet the threshold is re-classified into the UG cluster. It should be noted that the CurrGr cluster may in fact not actually shrink if at least one candidate meets or exceeds the threshold. However, the ICR may be updated if one of those candidates is a reference candidate that replaces the corresponding initial reference.

Similarly, the CurrGr cluster may shrink because candidates (both the initial reference and the reference candidates) of at least one segmented block does not meet the threshold while the ICR remains the same or not updated because for each block that meets or exceeds the threshold it is the initial reference that is the optimal reference candidate. Another scenario may include a CurrGr which does not shrink and an ICR which is not updated.

In the case where CurrGr does shrink and the ICR is updated to the UCR, the shrinking process is followed by a growing process in which the processing system 32 is configured to compare the candidates of each of the segmented block in UG cluster to the UCR. The processing system determines the reference candidates for each segmented block in the UG cluster and compares the 2L+1 candidates to the UCR based on a similarity index or the like. Similarly to the shrinking process, if any of the candidates meet the threshold of the similarity index, the corresponding block is reclassified back into the CurrGr cluster based on the UCR. In addition, if the candidate with the maximum similarity to the UCR is one of the reference candidates rather than the initial reference, the initial reference is replaced with the max. similarity reference candidate, the segmentation of the corresponding block is shifted accord to the temporal location of the reference candidate relative to the initial candidate, and the UCR is updated based on the temporally shifted block. The growing and shrinking processes are repeated until the CurrGr and the UG clusters have stabilized or reached steady state, i.e. no more segmented block can be re-classified and the ICR or UCR can no longer be updated.

Once steady state is achieved, the processing system 32 labels the CurrGr cluster as a clustered group, e.g. a first cluster, and is parked aside. Any remaining blocks unclassified blocks in the UG cluster are assigned to a newly initialized CurrGr and the UG cluster is set to empty. The processing system repeats the process of determining an ICR for the new CurrGr cluster and performing the shrinking and growing processes until steady state between the new CurrGr and the UG clusters is achieved. At which point, the CurrGr is labeled as a subsequent clustered group, e.g. a second cluster, and the remaining unclassified blocks in the UG cluster are assigned to a newly initialized CurrGr and UG is emptied. Subsequent grouped clusters, e.g. a third cluster, fourth cluster, fifth cluster, etc., are determined until there remains no unclassified segmented block in the UG cluster. It should be noted that in some instances some of the clustered groups may include only one segmented block and in other instances some of the segmented blocks may not be classifiable into a cluster.

In some embodiments, the processing system 32 is configured to identify the heart beats (or other physiological instance), i.e. segment the data stream of activation signals according to subsequent heart beats, in selected individual channels of mapping electrodes 24 or a subset of mapping electrodes which pertain to sub-region of the anatomical structure which exhibits a higher prevalence of similar heart beat types or heart beat patterns. Sub-regions of the heart may exhibit a higher prevalence of similar heart beat patterns or types pertaining to a core of a rotor or foci of aberrant activity related to a fibrillation.

In some embodiments, the system 10 may include a user interface in which a user can input parameters such as the maximum lag L, a threshold value, the comparison algorithm used to determine a similarity index or measure, the type of characteristic representation used to represent the CurrGr cluster, and the like. After the processing system 32 has finished clustering the segmented blocks into at least one clustered group or into various clustered groups and the optimal reference for each heart beat (or other physiological instance) is determined, the processing system can display on the display device 40 a summary plot or a summary of the clustered groups, their corresponding ICR or UCR, unclassifiable segmented blocks, prevalent or common patterns, In some embodiments, the processing system 32 can identify the most prevalent patterns. For example, a user may instruct the system 10 to display the top M most common or prevalent patterns on the display 40 and the processing system will identify which M clustered groups have the most segmented blocks, e.g. heart beats, classified to the corresponding cluster and display to the user via the display device 40.

In another embodiment, the user may instruct the system 10 via a user interface to display a measure of variability in each clustered group. The processing system 32 can determine a measure of variability for each clustered group or a selected clustered group. The processing system is also configured to break up a clustered group into sub-groups for further evaluation based on the determined measure of variability.

In another embodiment, the processing system 32 is configured to determine a measure of variability of the unclassified segmented blocks or heart beats and display the variability on the display device 40. The determined measure of variability may be related to the randomness of the data set of activation signals and can be a useful quantification for developing a diagnosis for the heart or other anatomical structure.

Figure 6A:
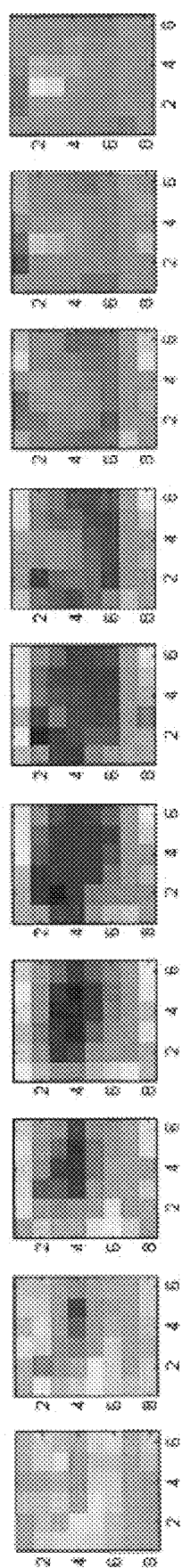
FIGS. 6A & 6B illustrate plots of prevalent patterns identified according to the system of FIG. 1.
Figure 6B:
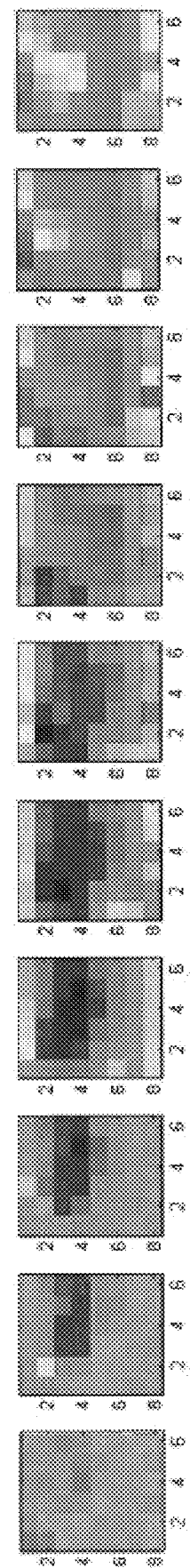

FIGS. 6A and 6B illustrate two identified optimized clusters with a prevalence measure of 34% and 7%, respectively. The optimized clusters are related to prevalent patters in the data stream of activation signals. The plots illustrated in both FIGS. 6A and 6B are based on the same data set used to generate FIG. 4. As illustrated in FIG. 4, the same identified patterns exhibit a prevalence of 40.6977% and 6.2016%. The discrepancies in pattern identification and associated prevalence in the various embodiments can be used in concert to further identify or eliminate target regions in the anatomical structure for therapy.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac mapping system for diagnosing and treating pathologies in a heart, the system comprising:
a plurality of mapping electrodes disposed in the heart configured to detect activation signals of physiological activity in the heart, each of the plurality of mapping electrodes having an electrode location;
a processing system associated with the plurality of mapping electrodes, the processing system configured to record the detected activation signals and associate one of the plurality of mapping electrodes with each recorded activation signal, the processing system further configured to determine a dominant frequency at each electrode location, and determine a wavefront vector at each electrode location based on a difference between the dominant frequency at a first electrode location and the dominant frequency at neighboring electrode locations;
wherein the processing system is further configured to:
generate a plurality of pattern maps, and wherein, to generate the plurality of pattern maps, the processing system is further configured to generate a pattern map for each sensed activation signal, each pattern map having the wavefront vector at each electrode location;
classify at least some of the plurality of pattern maps into distinct groups based on a percentage of pattern maps within each group having a particular similarity measure;
identify unclassified pattern maps that are not classified into any groups of similar patterns; and
determine a measure of variability of the detected activation signals based on the unclassified pattern maps; and
a display operatively coupled to the processing system to display one or more of the plurality of pattern maps including the wavefront vector at each electrode location and to display the measure of variability of the detected activation signals for diagnosing and treating pathologies in the heart.

2. The anatomical mapping system according to claim 1, wherein the processing system is further configured to determine a characteristic representation of one or more similarity measures, and display a summary plot of the characteristic representations.

3. The anatomical mapping system according to claim 1, wherein the processing system is further configured to generate the similarity measure based on each unique pair of identified pattern maps generated, which are based on a correlation of the corresponding patterns.

4. The anatomical mapping system according to claim 3, wherein the similarity measure is a correlation coefficient between each unique pair of pattern maps.

* * * * *